United States Patent [19]

Alanko et al.

[11] 4,348,532

[45] Sep. 7, 1982

[54] MONOORGANOSILOXY CONTAINING SILOXANE FLUIDS

[75] Inventors: Allan M. Alanko; Ollie W. Marko; Charles E. Skinner, all of Carrollton; Larry H. Wood, Campbellsburg, all of Ky.

[73] Assignee: Dow Corning Corporation, Midland, Mich.

[21] Appl. No.: 308,341

[22] Filed: Oct. 5, 1981

[51] Int. Cl.$^3$ ............................. C07F 7/08; C07F 7/18
[52] U.S. Cl. .................................. 556/457; 556/456; 556/460
[58] Field of Search ....................... 556/457, 460, 456

[56] References Cited

U.S. PATENT DOCUMENTS 4,108,882  8/1978  Mahone .............................. 556/460

Primary Examiner—Paul F. Shaver
Attorney, Agent, or Firm—Jack E. Moermond

[57] ABSTRACT

Organosiloxane fluids containing polyfunctional silicon atoms are made by reacting a mixture of chlorosilanes containing a silane or disilane having at least 3 chlorine atoms with methanol in contact with certain quaternary ammonium halide catalysts. For example a fluid methylpolysiloxane was obtained by reacting a mixture of 30 weight percent methyltrichlorosilane and 70 weight percent dimethyldichlorosilane with methanol in contact with methyl pyridinium chloride.

5 Claims, No Drawings

MONOORGANOSILOXY CONTAINING SILOXANE FLUIDS

BACKGROUND OF THE INVENTION

U.S. Pat. No. 4,108,882 shows a method of preparing siloxanes by reacting chlorosilanes with methanol in the presence of quaternary ammonium catalysts. The virtue of this process is that in one step one can go from a chlorosilane to a siloxane and produce methylchloride which is a useful intermediate in the preparation of methylsiloxanes. Also, the process has the virtue of producing very little dimethylether. The primary object of this patent was to produce high yields of cyclic diorganosiloxanes. Therefore, the patent is limited to either diorganochlorosilanes or triorganochlorosilanes and there is no teaching therein of the incorporation of any monoorganotrichlorosilane in the starting materials. One might expect that the incorporation of monoorganotrichlorosilanes in the reaction mixture would cause gellation and would thereby reduce the formation of the desired cyclics and produce an inefficient process. The latter is particularly true since the formation of gels in the reactor would interfere with the activity of the catalyst.

Fluids containing monoorganosiloxanes are desirable for many applications. For example, the incorporation of 3 to 4 mol percent monomethylsiloxane in a fluid containing dimethylsiloxane reduces the glass transition temperature from approximately $-40°$ C. to $-100°$ C. There are many applications in which such low temperature stability is required. Furthermore, the incorporation of significant amounts of monomethylsiloxane in a diorganosiloxane fluid increases the specific gravity. In some applications, particularly in the electrical area, it is desirable to have a diorganopolysiloxane fluid with a specific gravity above 1 so that water will float to the top of the fluid. This makes the water much more easily removed from the system.

It is the object of this invention to produce monoorgano containing polysiloxane fluids by a method which gives excellent yields of such fluids essentially free of gels. It is also the object to carry out the procedure by a manner which produces methylchloride containing small amounts of dimethyl ether.

BRIEF DESCRIPTION OF THE INVENTION

This invention relates to a method for preparing siloxanes and methylchloride by reacting methanol with chlorosilanes in contact with a quaternary ammonium catalyst of the group consisting of:

(1) pyridinium chlorides of the formula

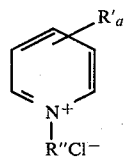

(2) compounds of the formula $R'''_4N^+Cl^-$,

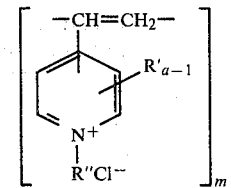

and

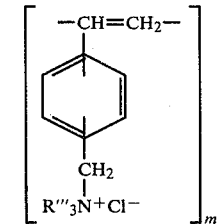

where $R'$ is a hydrocarbon radical having 18 or less carbon atoms; "a" is an integer from 0-5; "m" is an integer greater than 1, $R''$ is a lower alkyl radical; and $R'''$ is selected from the group consisting of methyl, hydroxy alkyl of 2-4 inclusive carbon atoms, aromatic hydrocarbon radicals, and $ArCH_2-$ radicals in which Ar is an aromatic hydrocarbon radical there being no more than 18 carbon atoms total in the $R'''$ group, the improvement comprising employing as the chlorosilanes a mixture of $R_2SiCl_2$ and a chlorosilane selected from the group consisting of $RSiCl_3$ and $R_nCl_{3-n}SiSiR_{n'}Cl_{3-n'}$ and optionally $R_3SiCl$ in which mixture there is from 2 to 50 weight percent of a silane containing at least 3 chlorine atoms per molecule based upon the total weight of chlorosilanes in the mixture, said reaction being carried out at a temperature of at least about 100° C. and under a temperature-pressure relationship such that water escapes from the reaction zone, whereby stable polysiloxane fluids are obtained, in said silanes R is methyl, ethyl, 3-chloropropyl, or 3,3,3-trifluoropropyl and n and n' are each integers from 0 to 2, the total value of n and n' being from 1 to 3.

The term "stable" is based on the fact (see Example 2) that the fluid can be treated with 15% hydrochloric acid and then heated at 180° C. for one hour without gellation and with a relatively small increase in viscosity. The latter is probably due to silanol condensation.

Any quaternary ammonium compound within the scope of U.S. Pat. No. 4,108,882 (which is hereby incorporated in its entirety by reference) can be used in this invention. Particular attention is directed to column 2, line 1 through col. 3, line 8 of the aforesaid patent together with the catalyst shown in Examples 4 to 7 and 11 to 14 inclusive. As stated in said patent the catalyst can be added as such or be prepared in situ.

Any chlorosilane of the above formulae in which R is methyl, ethyl, 3-chloropropyl or 3,3,3-trifluoropropyl can be used in this invention. Specific examples of such silanes are methyltrichlorosilane, dimethyldichlorosilane, trimethylmonochlorosilane, methylethyldichlorosilane, ethyldimethylmonochlorosilane, ethyltrichlorosilane, diethyldichlorosilane, 3-chloropropylmethyldichlorosilane, 3-chloropropyltrichlorosilane, 3,3,3-trifluoropropylmethyldichlorosilane and 3,3,3-trifluoropropyltrichlorosilane. Operative disilanes are, for example, $(CH_3)_2ClSiSi(CH_3)Si_2$, $(CH_3)Cl_2SiSiCl_2(CH_3)$, $(CH_3)Cl_2SiSiC_2H_5Cl_2$ and $Cl_3SiSi(CH_3)Cl_2$.

For the purpose of this invention the chlorosilane mixture must contain from 2 to 50 percent by weight of a polyfunctional silane based on the total weight of the chlorosilane mixture. The term "polyfunctional silane" means the silane contains at least three chlorine atoms per molecule. When the amount of polyfunctional silane exceeds 50 percent by weight, separation of the siloxane residue and the catalyst is not feasible without resorting to solvent extraction.

Proportions of chlorosilane to methanol are not critical. Obviously, the best yields of siloxane fluids and methyl chloride will be obtained when the two reactants are approximately stoichiometric. Preferably the methanol is employed in amounts of from 5 to 10% mol excess based on the total silicon-bonded chlorine.

The rate of addition of the chlorosilanes and alcohol is not critical.

The reaction can be carried out at pressures ranging from subatmospheric to 150 psi and the temperature from 100° C. or less to 180° C. The pressure/temperature relationship should be such that water is removed from the reaction vessel. Otherwise the catalyst will be diluted to a point where it will no longer function. In other words the system tends to revert to a normal hydrolysis.

The reaction can be carried out in any convenient manner as shown in the aforesaid patent. The best way known to applicants is to operate a continuous reaction in which the catalyst and non-volatile siloxanes are removed from the reaction zone, separated and the catalyst continuously recycled into the reaction zone.

The products of this reaction are composed of a volatile portion composed of cyclic siloxanes, methyl chloride, water and unreacted starting materials and a non-volatile residue composed of siloxane fluids which can be linear or cyclic in nature and contain residual methoxy groups. The proportion of volatiles decreases with increasing pressure and with increasing polyfunctional silane content in the starting mixture.

The following examples are illustrative only and should not be construed as limiting the invention which is properly delineated in the appended claims. In addition to the specific catalyst and silanes shown in the examples, anyone skilled in the organosilicon technology would know that any catalyst and any silane within the scope of the disclosure would operate in the present invention.

EXAMPLE 1

This example shows the practical upper limit of the amount of polyfunctional silane in the mixture. The reactor volume was 120 ml.

In each run a mixture of chlorosilanes and methanol in the ratio of 1.1 mols of methanol per mol of silicon-bonded chlorine were sparged through molten methyl pyridinium chloride at a rate such that 1.1 volumes of reaction mixture per volume of molten catalyst passed through the reactor per hour. The reactions were each carried out at atmospheric pressure and at 140° C. As the reaction proceeded cyclic siloxanes, methyl chloride, water and unreacted methanol distilled overhead. A mixture of catalyst and linear siloxane residue were continuously removed from an overflow port, allowed to separate and the catalyst returned to the reactor. The results were shown in the table below:

| Run | Percent By Weight $CH_3SiCl_3$ | Percent By Weight $(CH_3)_2SiCl_2$ | Percent Chloride Efficiency* | Phase Separation | Percent Volatiles By Weight | Percent By Weight Residue |
|---|---|---|---|---|---|---|
| 1 | 10 | 90 | 89 | excellent | 73 | 27 |
| 2 | 30 | 70 | — | excellent | 37 | 63 |
| 3 | 50 | 50 | 88 | good | 29 | 71 |
| 4** | 67 | 30 | — | poor | 5 | 95 |

*Chloride efficiency can be increased by employing 2 or more reactors in series. The efficiency is the percent of SiCl where is converted to methylchloride.
**Included for purposes of comparison.

EXAMPLE 2

The mixed chlorosilanes shown below were reacted with methanol in the manner of Example 1 except that the ratio of methanol to silicon-bonded chlorine was 1.05 to 1 and the rate of addition was 1 volume per hour of reactants per volume of molten catalyst. Runs 1–4 were made at 150° C. and 40 psi pressure. Run 5 was made at 145° C. and atmospheric pressure. The residue from the reaction was stripped*, in each case, at 180° C. at 10 mm pressure for 1 hour and the viscosity of the stripped residue was determined. The results are shown in the table below.

*The residues from runs 1 and 2 were each divided into two parts. One part was stripped to give the viscosity shown in the tables. The second part of each was treated with acid as shown below and then stripped.

| Run No. | Percent Weight Chlorosilanes $CH_3SiCl_3$ | $(CH_3)_2SiCl_2$ | $(CH_3)_3SiCl$ | Percent Chloride Efficiency | Percent Volatiles By Weight | Stripped By Weight Residue | Viscosity of Residue in cs at 25° C. |
|---|---|---|---|---|---|---|---|
| 1 | 25 | 75 | 0 | 97 | 21 | 79 | 57 |
| 2 | 25 | 72 | 3 | — | 27 | 73 | 59 |
| 3 | 10 | 90 | 0 | 94 | 27 | 73 | 57 |
| 4 | 10 | 87 | 3 | 93 | — | — | 40 |
| 5 | 25 | 71 | 4 | — | 25 | 75 | 0.49 |

Part of the residue from Run 1, prior to stripping, was stirred with an equal volume of 15 percent by weight aqueous HCl at 50° C. for 1 hour. The product was then washed with an equal volume of water at 50° C. for 1 hour. The resulting material was heated at 180° C. at 10 mm pressure for one hour to remove volatiles. The resulting residue had a viscosity of 580 cs at 25° C. as compared with 57 cs for the original residue.

Part of the residue from Run 2 was treated in a like manner except that the product was heated with stirring with the aqueous HCl for 2 hours. After removal of the volatiles the remaining fluids had a viscosity of 80 cs at 25° C. as compared with 59 cs for the fluid that was stripped without acid treatment.

EXAMPLE 3

The conditions of Example 1 were repeated except that the silane mixture had the composition in percent by weight 20 $(CH_3)_2SiCl_2$, 10 $C_2H_5(CH_3)_2SiCl$, 10 $C_2H_5(CH_3)SiCl_2$, 40 percent heptane and 20 $(CH_3)_2ClSiSiCl_2(CH_3)$.

Separation of the residue and catalyst was excellent. The chloride efficiency was 96 percent and the ratio of volatiles to residue was 70 to 30. The residue was a fluid.

EXAMPLE 4

Vapors of a mixture 93 percent by weight dimethyldichlorosilane, 4.5 percent methyltrichlorosilane and 2.5 percent by weight trimethylmonochlorosilane together with the vapors of methanol in amount of 10 percent mol excess over the amount of silicon-bonded chlorine, were sparged through 10 ml of molten methyl pyridinium chloride at the rate of 98 cc of mixture over a period of 4 hours and 40 minutes. The reaction was carried out at atmospheric pressure and at 140° C. During the reaction cyclic siloxanes distilled from the reactor and a liquid residue which contained no gel formed in the reactor. The liquid residue was easily separatable from the molten catalyst.

EXAMPLE 5

The experiment of Example 4 was repeated except that the chlorosilane was a mixture of 94 weight percent dimethyldichlorosilane, 3.5 weight percent methyltrichlorosilane and 2.5 weight percent trimethylmonochlorosilane. Equivalent results were obtained.

That which is claimed is:

1. In a method for preparing siloxanes and methyl chloride by reacting methanol with chlorosilanes in contact with a quaternary ammonium catalyst of the group consisting of:

(1) pyridinium chlorides of the formula

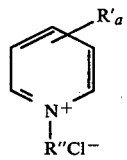

(2) compounds of the formula $R'''_4N^+Cl^-$,

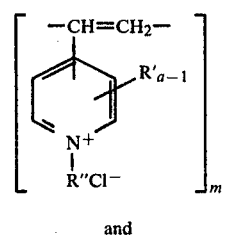

and

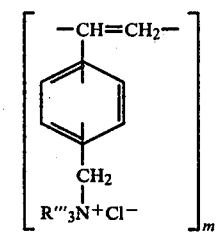

where R' is a hydrocarbon radical having 18 or less carbon atoms; "a" is an integer from 0–5; "m" is an integer greater than 1, R" is a lower alkyl radical; and R''' is selected from the group consisting of methyl, hydroxy alkyl of 2–4 inclusive carbon atoms, aromatic hydrocarbon radicals, and ArCH$_2$— radicals in which Ar is an aromatic hydrocarbon radical there being no more than 18 carbon atoms total in the R''' group, the improvement comprising employing as the chlorosilanes a mixture of $R_2SiCl_2$ and a silane (A) selected from the group consisting of $RSiCl_3$ and $R_nCl_{3-n}SiSiR_{n'}Cl_{3-n'}$ and optionally $R_3SiCl$ in which mixture there is from 2 to 50 percent by weight based upon the total weight of the chlorosilane mixture of a silane containing at least 3 chlorine atoms per molecule, said reaction being carried out at a temperature of at least about 100° C. and under temperature/pressure relationship such that water escapes from the reaction zone, whereby stable polysiloxane fluids are obtained, in said silanes R is methyl, ethyl, 3-chloropropyl, or 3,3,3-trifluoropropyl and n and n' are each integers from 0 to 2, the total value of n and n' being from 1 to 3.

2. The method of claim 1 in which the chlorosilane mixture and methanol are passed through a molten catalyst.

3. The method of claim 1 in which R is methyl.

4. The method of claim 2 in which R is methyl.

5. The method of claim 1 or 2 in which (A) is methyltrichlorosilane and the catalyst is methyl pyridinium chloride.

* * * * *

UNITED STATES PATENT AND TRADEMARK OFFICE
CERTIFICATE OF CORRECTION

PATENT NO. : 4,348,532
DATED : September 7, 1982
INVENTOR(S) : A.M. Alanko; O.W. Marko; C.E. Skinner & L.H. Wood It is certified that error appears in the above—identified patent and that said Letters Patent is hereby corrected as shown below:

In Column 4, in the Table; the line reading "The efficiency is the percent of SiCl where is converted to methylchloride." should read "The efficiency is the percent of SiCl which is converted to methylchloride."

UNITED STATES PATENT AND TRADEMARK OFFICE
CERTIFICATE OF CORRECTION

PATENT NO. : 4,348,532  
DATED : September 7, 1982  
INVENTOR(S) : A.M. Alanko; O.W. Marko; C.E. Skinner & L.H. Wood Page 2 of 2

It is certified that error appears in the above—identified patent and that said Letters Patent is hereby corrected as shown below:

In Column 4, in the Table; the column reading

" Stripped    should read    " Percent

By Weight

Residue".                     By Weight

Residue"

In Column 4, in the Table; the column reading

" Viscosity of    should read    " Viscosity of

Residue in cs                    Stripped at 25°C. "                    Residue in cs at 25°C. "

Signed and Sealed this

Twenty-second Day of March 1983

[SEAL]

Attest:

Attesting Officer

GERALD J. MOSSINGHOFF  
Commissioner of Patents and Trademarks